United States Patent
Albahkali et al.

(10) Patent No.: US 10,397,989 B1
(45) Date of Patent: Aug. 27, 2019

(54) OVEN WITH TEMPERATURE PROBE

(71) Applicant: KING SAUD UNIVERSITY, Riyadh (SA)

(72) Inventors: Thamer Ali Albahkali, Riyadh (SA); Hany Hassan Aly Sayed, Riyadh (SA); Mohamed Elsayed Mohamed Bassuni, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/251,294

(22) Filed: Jan. 18, 2019

(51) Int. Cl.
| | |
|---|---|
| *H05B 6/50* | (2006.01) |
| *H05B 6/64* | (2006.01) |
| *F24C 7/08* | (2006.01) |
| *H05B 1/02* | (2006.01) |
| *G01K 1/14* | (2006.01) |

(Continued)

(52) U.S. Cl.
CPC .......... *H05B 6/6452* (2013.01); *F24C 7/088* (2013.01); *G01K 1/14* (2013.01); *G01N 33/12* (2013.01); *H05B 1/0263* (2013.01); *G01K 2207/06* (2013.01)

(58) Field of Classification Search
CPC .... H05B 6/6411; H05B 6/6447; H05B 6/645; H05B 6/6452; H05B 6/66; H05B 6/74; H05B 1/0263; F24C 7/02; F24C 7/08; F24C 7/087; F24C 7/088; G01K 1/00; G01K 1/08; G01K 1/14; G01K 1/146; G01K 2207/06; G01N 33/12
USPC ............. 219/446.1, 448.11, 448.14, 448.15, 219/448.16, 448.18, 448.19, 627, 667, 219/710, 711, 712, 713
See application file for complete search history.

(56) References Cited

U.S. PATENT DOCUMENTS

| 2,989,259 A | 6/1961 | Youhouse et al. |
| 4,038,510 A * | 7/1977 | White ................. H05B 6/6452 219/712 |

(Continued)

FOREIGN PATENT DOCUMENTS

| CN | 102297462 A | 12/2011 |
| GB | 1491739 A | 11/1977 |

OTHER PUBLICATIONS

General Tools & Instruments Replacement Telescoping Hot Wire Air Speed—Temperature Probe for #HWA4204HA; printed from https://www.generaltools.com/replacement-telescoping-hot-wire-air-speed-temperature-probe-for-hwa4204ha on Dec. 27, 2018.

*Primary Examiner* — Hung D Nguyen
(74) *Attorney, Agent, or Firm* — Richard C. Litman

(57) ABSTRACT

The oven with a temperature probe measures the temperature of food being cooked within the oven to provide real time feedback for determining a status of the food being cooked, such as, for example, indications that the food is fully cooked, partially cooked or uncooked. The oven with a temperature probe is similar to a conventional oven, but with a telescopic tube which selectively extends into the cooking chamber of the oven. An upper end of the telescopic tube is mounted within an open interior of a hollow upper wall of the oven, and a lower end of the telescopic tube defines a probe tip, containing a temperature sensor for measuring an internal temperature of the food being cooked. When not in use, the telescopic tube collapses fully within the open interior of the hollow upper wall. A display indicates cooking status of the food, based on the measured temperature.

20 Claims, 4 Drawing Sheets

(51) Int. Cl.
*G01N 33/12* (2006.01)
*H05B 3/68* (2006.01)

(56) References Cited

U.S. PATENT DOCUMENTS

| | | | | |
|---|---|---|---|---|
| 4,149,056 | A | * | 4/1979 | Kaneshiro ................ G01K 1/00 219/712 |
| 4,588,377 | A | * | 5/1986 | Kohn .................... G01K 1/146 266/99 |
| 4,691,087 | A | * | 9/1987 | Lee ..................... H05B 6/6411 219/712 |
| 4,747,712 | A | * | 5/1988 | Gonoh ................. H05B 6/6411 219/712 |
| 5,043,547 | A | | 8/1991 | Lee |
| 10,006,817 | B2 | | 6/2018 | Swayne et al. |
| 2010/0006558 | A1 | | 1/2010 | McLoughlin et al. |
| 2017/0167733 | A1 | | 6/2017 | Böckler et al. |
| 2018/0143083 | A1 | | 5/2018 | Pastore et al. |
| 2019/0064001 | A1 | * | 2/2019 | Valdez .................. G01K 1/146 |

\* cited by examiner

OVEN WITH TEMPERATURE PROBE

BACKGROUND

1. Field

The disclosure of the present patent application relates to the cooking of foodstuffs, and particularly to an oven with an integrated temperature probe for measuring the temperature of food being cooked in the oven.

2. Description of the Related Art

Conventional temperature probes for monitoring the temperature of food being cooked or baked in ovens typically include a conventional temperature thermoelectric sensor which is inserted into the food and remains inserted throughout the cooking process. When conventional temperature probes are used in conjunction with soft foods or rising foods, such as bread loafs, cakes and souffles, they tend to fail because the probe tip moves away from the ideal position, leading to unstable temperature readings. In some cases, the probe may eventually fall out of the food, thus leading to completely unreliable measurements. For these reasons, such conventional temperature probes are typically limited in their usage to only measuring temperatures in meat and fish whose stiffness keeps the probe in place throughout the entire cooking process. Thus, an oven with a temperature probe solving the aforementioned problems is desired.

SUMMARY

The oven with a temperature probe measures the temperature of food being cooked within the oven to provide real time feedback for determining a status of the food being cooked, such as, for example, indications that the food is fully cooked, partially cooked or uncooked. The oven with a temperature probe is similar to a conventional oven, including a housing having an upper wall, a lower wall, at least one sidewall and an open front end which is covered by a door. The housing defines a cooking chamber for receiving food to be cooked therein. It should be understood that the oven may be any type of conventional oven with any suitable components for cooking the food, such as, for example, a microwave oven, an oven with electrical heating elements, a gas oven, a convection oven or the like.

The upper wall of the housing is hollow and has an upper panel and a lower panel with an open interior region being defined therebetween. An opening is formed through the lower panel such that the open interior region is in communication with the cooking chamber. A cover is mounted, e.g., pivotally mounted, to the lower panel of the upper wall of the housing, such that the cover can selectively cover the opening formed through the lower panel.

An upper end of a telescopic tube is mounted on the upper panel of the upper wall of the housing, such that, in a collapsed state, the telescopic tube is contained within the open interior region of the upper wall, and in an extended state, the telescopic tube extends through the opening formed through the lower panel and into the cooking chamber. The lower end of the telescopic tube defines a probe tip, with a temperature sensor being mounted therein. A probe motor mounted within the open interior region of the upper wall selectively drives collapse and extension of the telescopic tube.

A controller is in electrical communication with the temperature sensor for receiving temperature measurements therefrom. The temperature measurements represent the internal temperature of the food received within the cooking chamber when the telescopic tube is extended such that the probe tip is inserted into the food. The controller is also in electrical communication with the probe motor for selectively controlling the collapse and extension of the telescopic tube. A control panel is mounted to the housing and includes a display and a user interface. The display and user interface are in electrical communication with the controller for displaying the internal temperature of the food and for providing a programmable interface with cooking status feedback.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
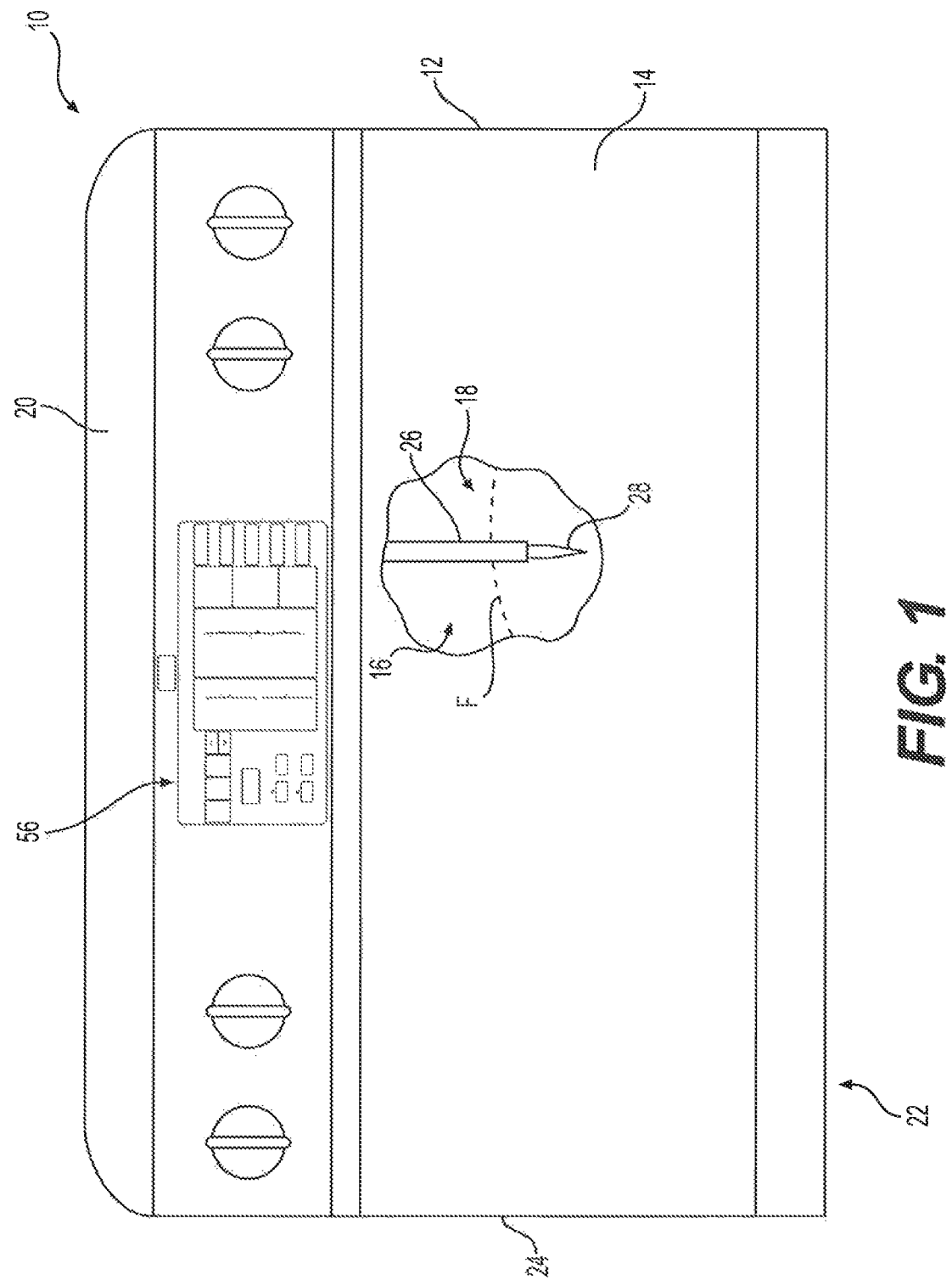
FIG. 1 is a partially cut away front view of an oven with a temperature probe.

Referring now to FIG. 1, the oven with a temperature probe 10 measures the temperature of food F being cooked within the oven to provide real time feedback for determining a status of the food F as it is cooked. As will be described in greater detail below, these indications may be presented to the user on control panel 56, indicating, for example, that the food is fully cooked, partially cooked or uncooked. As shown, the oven with a temperature probe 10 is similar to a conventional oven, including a housing 12 having an upper wall 20, a lower wall 22, at least one sidewall 24 and an open front end which is covered by a door 14. The housing 12 defines a cooking chamber 18 for receiving food F to be cooked therein. It should be understood that the oven may be any type of conventional oven with any suitable means or components for selectively cooking the food, such as, for example, microwave radiation, electrical, or gas heating components. It should be further understood that the overall configuration of oven 10, as shown in FIG. 1, is shown for exemplary purposes only.

Figure 2:
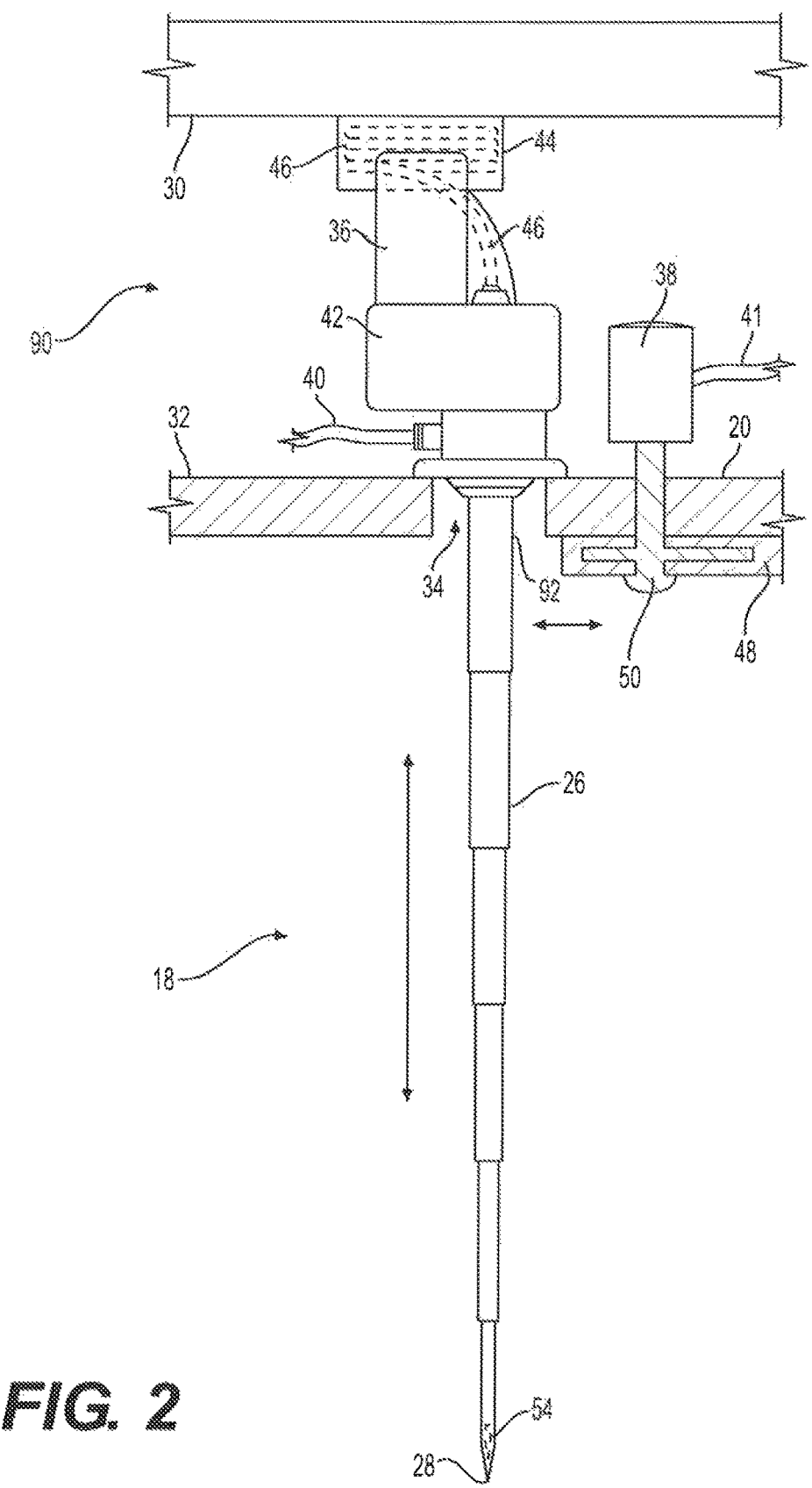
FIG. 2 is a partial front view in partial section of the oven with a temperature probe.

As shown in FIG. 2, the upper wall 20 of housing 12 is hollow and has an upper panel 30 and a lower panel 32, with an open interior region 90 being defined therebetween. An opening 34 is formed through the lower panel 32 such that the open interior region 90 is in communication with the cooking chamber 18. A cover 48 is pivotally mounted to the lower panel 32 of the upper wall 20, such that the cover 48 can selectively cover the opening 34.

An upper end 92 of a telescopic tube 26 is mounted on the upper panel 30 of the upper wall 20, such that, in a collapsed state, the telescopic tube 26 is contained within the open interior region 90 of upper wall 20. In its extended state, as shown in FIG. 2, the telescopic tube 26 extends through the opening 34 formed through the lower panel 32 and into the cooking chamber 18. The lower end 28 of the telescopic tube defines a probe tip, with a temperature sensor 54 being mounted therein. A probe motor 36 or other suitable driving mechanism is mounted within the open interior region 90 of upper wall 20 for selectively driving collapse and extension of telescopic tube 26. It should be understood that temperature sensor 54 may be any suitable type of temperature sensor, such as a thermocouple or the like. Telescopic tube 26 may be made from any suitable type of material which is sturdy enough to penetrate food F without deformation and which is also resistant to damage from the heat within cooking chamber 18.

It should be understood that telescopic tube 26 may be made to selectively extend and collapse using a cable or other suitable extendable structure. As a non-limiting example, telescopic tube 26 may be cable-driven to selectively extend and collapse, as is well known in the field of automated extendable vehicle antennas. An example of such a system is shown in U.S. Pat. No. 2,989,259, which is hereby incorporated by reference in its entirety. In the non-limiting example of FIG. 2, when in the collapsed state, telescopic tube 26 is contained within chamber 42 for secure and stable reception and storage thereof. Cable 46, associated with the cable drive system, is received within receptacle 44 for extension and retraction during use.

It should be understood that cover 48 may be driven to selectively cover opening 34 by any suitable type of drive system. In the non-limiting example of FIG. 2, cover motor 38 is mounted within the open interior region 90 of upper wall 30. An axle 50 extends from cover motor 38, through lower panel 32, and cover 48 is mounted on an end thereof, within cooking chamber 18. Actuation of cover motor 38 drives axle 50 to rotate, thus driving pivotal rotation of cover 48.

Figure 3:
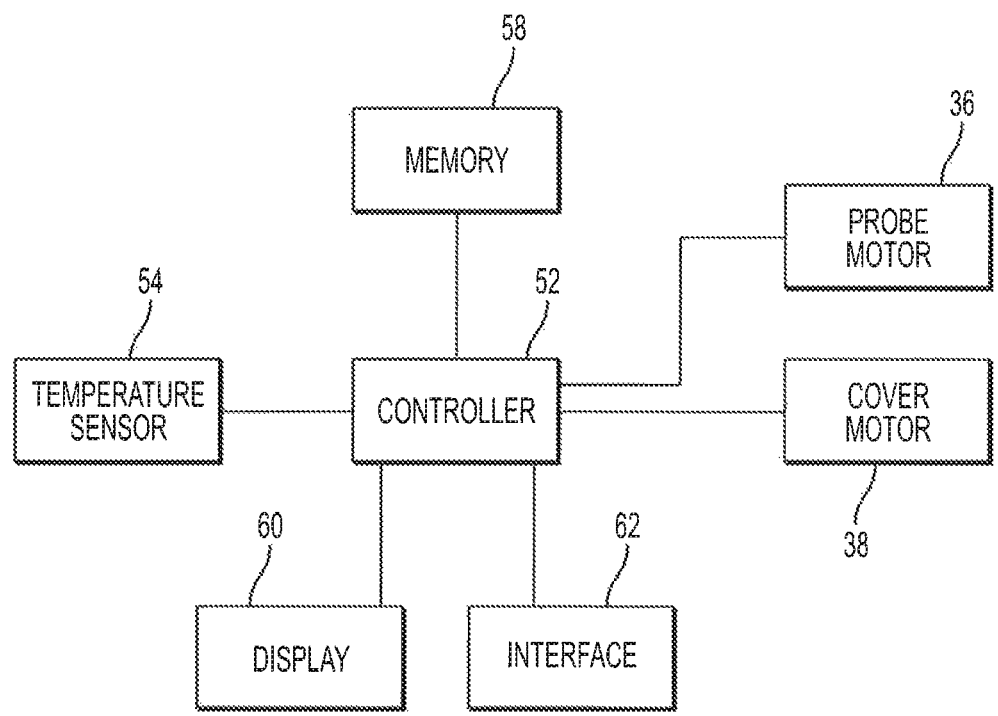
FIG. 3 is a block diagram showing components of a control system for the oven with a temperature probe.

As shown in FIG. 3, a controller 52 is in electrical communication with the temperature sensor 54 for receiving temperature measurements therefrom. It should be understood that controller 52 may be any suitable type of controller, such as a processor, programmable logic controller or the like. The temperature measurements represent the internal temperature of the food F received within the cooking chamber 18 when the telescopic tube 26 is extended such that the probe tip 28 is inserted into food F. The controller 52 is also in electrical communication with the probe motor 36 (via wire or cable 40 of FIG. 2) for selectively controlling the collapse and extension of the telescopic tube 26. Additionally, cover motor 38 is also in electrical communication with controller 52 (via wire or cable 41 of FIG. 2). As will be discussed in greater detail below, the controller 52 is also in electrical communication with a display 60 and a user interface 62, which are integrated into control panel 56. Non-transitory computer readable memory 58 is associated with controller 52 for containing a database of desired cooking temperatures and times associated with a variety of different foods, allowing the user to program (via user interface 62) oven 10 for particular types of food.

In use, when the temperature of food F is not being measured, the telescopic tube 26 is in its fully collapsed state, contained within chamber 42 within open interior region 90 of upper wall 20, and the cover 48 is in a closed position. In the closed position, cover 48 fully covers the opening 34 formed through the lower panel 32 of the upper wall 20, providing a continuous and solid upper surface for the cooking chamber 18, similar to that of a conventional oven. When the telescopic tube 28 is extended, the cover 48 is pivoted into an open state, as shown in FIG. 2, allowing the telescopic tube 26 to freely extend into the cooking chamber 18. Cover 48 is preferably formed from the same, or similar, material as that of lower panel 32, protecting telescopic tube 26 and open interior region 90 from the heat of the cooking chamber 18.

Figure 4:
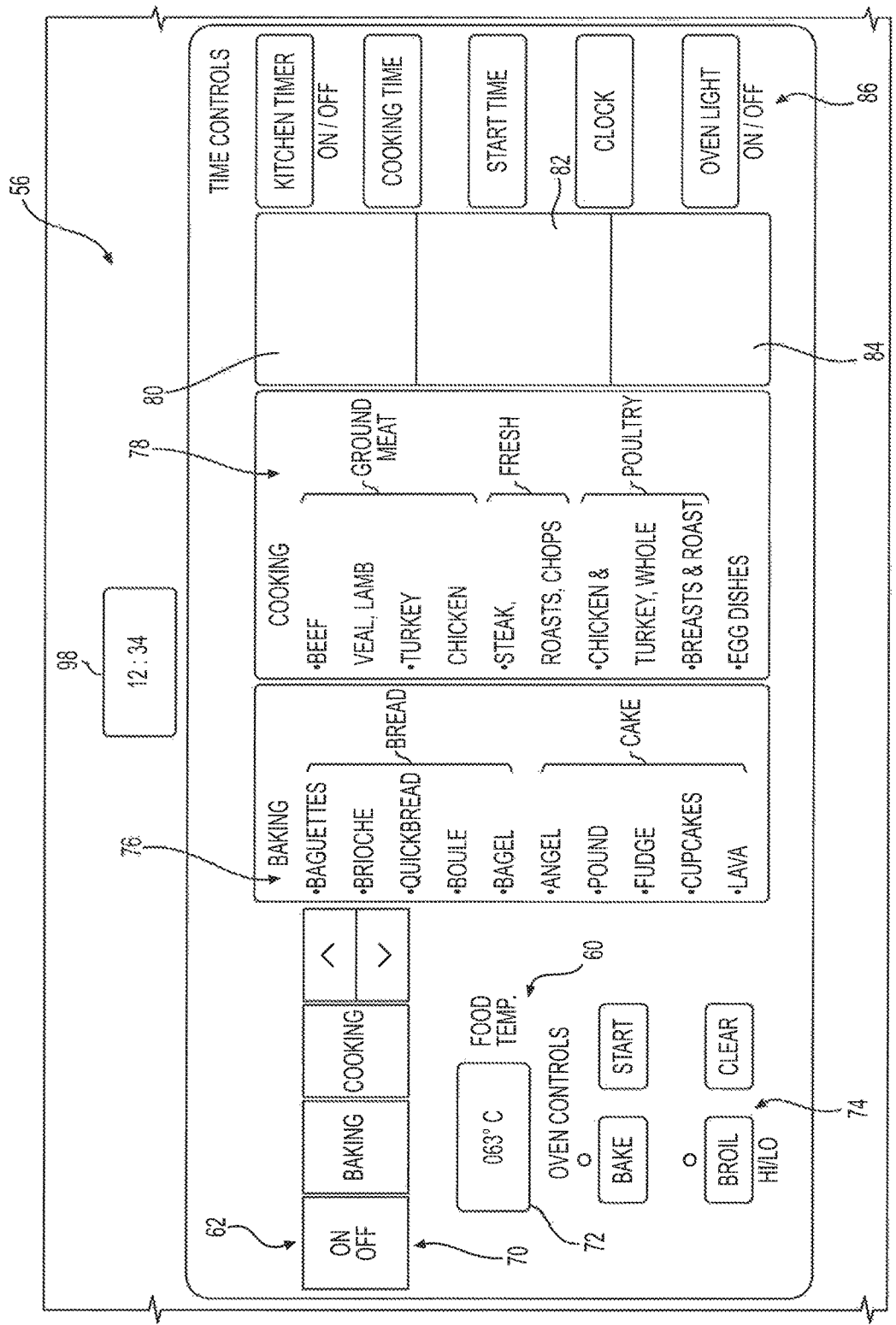
FIG. 4 is a partial front view of the oven with a temperature probe showing a control panel thereof.

As best shown in FIG. 4, the control panel 56, which is mounted to the housing 12, includes both a general display 60 and a user interface 62. The display 60 and user interface 62 are in electrical communication with the controller 52 for displaying the internal temperature of the food F and for providing a programmable interface with cooking status feedback. The display 60 may include conventional display elements, such as an indicator of the measured temperature 72 and a clock and/or timer 98. Additionally, cooking status indicators 80, 82, 84 are provided for indicating the cooking status of food F. As a non-limiting example, indicator 80 may be a red light emitting diode (LEI)), indicator 82 may be a yellow LED, and indicator 84 may be a green LED. Red indicator 80 would light when temperature sensor 54 provides an internal temperature measurement which controller 52 (in conjunction with the database stored in memory 58) determines to represent "uncooked". Yellow indicator 82 would light to indicated "partially cooked", and green indicator 84 would light to indicate "fully cooked".

The user interface 62 may include conventional oven controls 70, 74, 86, along with additional programmable backing controls 76 and cooking controls 78 (shown here as non-limiting examples). The programmable controls 76, 78 allow the user to input the type of food F being cooked or baked, thus allowing controller 52 to determine the proper cooking temperature thereof. It should be understood that the conventional buttons and display elements of control panel 56 are shown in FIG. 4 for exemplary purposes only, and may include any suitable type of displays, such as LEDs, liquid crystal displays or the like, and any suitable type of interface elements, such as buttons, switches or the like. As a further example, the display 60 and user interface 62 may be integrated into a single touchscreen panel.

It should be understood that telescopic tube 26 may be deployed manually, through input by the user on user interface 62, or may be deployed automatically under the control of controller 52. Additionally, it should be understood that the extent of expansion of telescopic tube 26 (i.e., the depth of penetration of probe tip 28 within food F) may also be deployed manually, through input by the user on user interface 62, or may be deployed automatically under the control of controller 52.

It is to be understood that the oven with a temperature probe is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. An oven with a temperature probe, comprising:
   a housing having an upper wall, a lower wall, at least one sidewall and an open front end, the housing defining a cooking chamber for receiving food to be cooked therein, wherein the upper wall is hollow and has an upper panel and a lower panel with an open interior region being defined therebetween, an opening being formed through the lower panel such that the open interior region is in communication with the cooking chamber;
   a door for selectively covering the open front end of the housing;

means for selectively cooking the food received within the cooking chamber;

a telescopic tube having opposed lower and upper ends, the lower end defining a probe tip and the upper end being mounted on the upper panel of the upper wall of the housing, whereby in a collapsed state, the telescopic tube is contained within the open interior region of the upper wall, and in an extended state, the telescopic tube extends through the opening formed through the lower panel and into the cooking chamber;

a temperature sensor mounted in the probe tip;

a driving mechanism for selectively driving collapse and extension of the telescopic tube; and a controller in electrical communication with the temperature sensor for receiving temperature measurements therefrom, the temperature measurements being associated with an internal temperature of the food received within the cooking chamber when the telescopic tube is extended such that the probe tip is inserted into the food, the controller being in further electrical communication with the driving mechanism for driving collapse and extension of the telescopic tube for providing control signals thereto.

2. The oven with a temperature probe as recited in claim 1, wherein the driving mechanism for selectively driving collapse and extension of the telescopic tube comprises a probe motor mounted within the open interior region of the upper wall.

3. The oven with a temperature probe as recited in claim 1, further comprising a cover mounted to the lower panel of the upper wall of the housing, the cover selectively covering the opening formed through the lower panel.

4. The oven with a temperature probe as recited in claim 3, further comprising a cover motor mounted within the open interior region of the upper wall for driving selective rotation of the cover.

5. The oven with a temperature probe as recited in claim 4, wherein the cover motor is in electrical communication with the controller.

6. The oven with a temperature probe as recited in claim 1, further comprising a display in electrical communication with the controller for displaying the internal temperature of the food.

7. The oven with a temperature probe as recited in claim 6, wherein the display further displays a cooking status associated with the food based on the internal temperature of the food.

8. An oven with a temperature probe, comprising:

a housing having an upper wall, a lower wall, at least one sidewall and an open front end, the housing defining a cooking chamber for receiving food to be cooked therein, wherein the upper wall is hollow and has an upper panel and a lower panel with an open interior region being defined therebetween, an opening being formed through the lower panel such that the open interior region is in communication with the cooking chamber;

a cover mounted to the lower panel of the upper wall of the housing, the cover selectively covering the opening formed through the lower panel;

means for selectively cooking the food received within the cooking chamber;

a telescopic tube having opposed lower and upper ends, the lower end defining a probe tip and the upper end being mounted on the upper panel of the upper wall of the housing, whereby in a collapsed state, the telescopic tube is contained within the open interior region of the upper wall, and in an extended state, the telescopic tube extends through the opening formed through the lower panel and into the cooking chamber;

a temperature sensor mounted in the probe tip;

a driving mechanism for selectively driving collapse and extension of the telescopic tube; and a controller in electrical communication with the temperature sensor for receiving temperature measurements therefrom, the temperature measurements being associated with an internal temperature of the food received within the cooking chamber when the telescopic tube is extended such that the probe tip is inserted into the food, the controller being in further electrical communication with the driving mechanism for selectively driving collapse and extension of the telescopic tube for providing control signals thereto.

9. The oven with a temperature probe as recited in claim 8, wherein the driving mechanism for selectively driving collapse and extension of the telescopic tube comprises a probe motor mounted within the open interior region of the upper wall.

10. The oven with a temperature probe as recited in claim 8, further comprising a cover motor mounted within the open interior region of the upper wall for driving selective rotation of the cover.

11. The oven with a temperature probe as recited in claim 10, wherein the cover motor is in electrical communication with the controller.

12. The oven with a temperature probe as recited in claim 8, further comprising a display in electrical communication with the controller for displaying the internal temperature of the food.

13. The oven with a temperature probe as recited in claim 12, wherein the display further displays a cooking status associated with the food based on the internal temperature of the food.

14. The oven with a temperature probe as recited in claim 8, further comprising a door for selectively covering the open front end of the housing.

15. An oven with a temperature probe, comprising:

a housing having an upper wall, a lower wall, at least one sidewall and an open front end, the housing defining a cooking chamber for receiving food to be cooked therein, wherein the upper wall is hollow and has an upper panel and a lower panel with an open interior region being defined therebetween, an opening being formed through the lower panel such that the open interior region is in communication with the cooking chamber;

a cover pivotally mounted to the lower panel of the upper wall of the housing, the cover selectively covering the opening formed through the lower panel;

means for selectively cooking the food received within the cooking chamber;

a telescopic tube having opposed lower and upper ends, the lower end defining a probe tip and the upper end being mounted on the upper panel of the upper wall of the housing, whereby in a collapsed state, the telescopic tube is contained within the open interior region of the upper wall, and in an extended state, the telescopic tube extends through the opening formed through the lower panel and into the cooking chamber;

a temperature sensor mounted in the probe tip;

driving mechanism for selectively driving collapse and extension of the telescopic tube;

a controller in electrical communication with the temperature sensor for receiving temperature measurements therefrom, the temperature measurements being associated with an internal temperature of the food received within the cooking chamber when the telescopic tube is extended such that the probe tip is inserted into the food, the controller being in further electrical communication with the driving mechanism for selectively driving collapse and extension of the telescopic tube for providing control signals thereto; and a display in electrical communication with the controller for displaying the internal temperature of the food.

16. The oven with a temperature probe as recited in claim 15, wherein the driving mechanism for selectively driving collapse and extension of the telescopic tube comprises a probe motor mounted within the open interior region of the upper wall.

17. The oven with a temperature probe as recited in claim 15, further comprising a cover motor mounted within the open interior region of the upper wall for driving selective rotation of the cover.

18. The oven with a temperature probe as recited in claim 17, wherein the cover motor is in electrical communication with the controller.

19. The oven with a temperature probe as recited in claim 17, wherein the display further displays a cooking status associated with the food based on the internal temperature of the food.

20. The oven with a temperature probe as recited in claim 15, further comprising a door for selectively covering the open front end of the housing.

* * * * *